United States Patent [19]

Marstrand

[11] 4,211,712

[45] Jul. 8, 1980

[54] COMPLEX COMPOUND FOR THE TREATMENT OF DISEASES DISCLOSING ABNORMAL BLOOD PICTURES

[76] Inventor: Even Marstrand, Humlebaek, Denmark

[21] Appl. No.: 865,416

[22] Filed: Dec. 29, 1977

[30] Foreign Application Priority Data

Jan. 17, 1977 [GB] United Kingdom ............... 01861/77

[51] Int. Cl.$^2$ ............................................. C07D 307/62
[52] U.S. Cl. .................................. 260/343.7; 424/245
[58] Field of Search ....................................... 260/343.7

[56] References Cited

U.S. PATENT DOCUMENTS

| | | | |
|---|---|---|---|
| 2,260,870 | 9/1934 | Ruskin | 260/343.7 |
| 2,995,495 | 8/1961 | Pancrazio et al. | 260/343.7 |
| 3,178,451 | 4/1965 | Reyes | 260/343.7 |

FOREIGN PATENT DOCUMENTS 805335 of 1936 France .
807877 of 1937 France .

OTHER PUBLICATIONS

Comptes Rendus des Seances Hebdomadaires de l'Academie des Sciences, 204 (1937), pp. 824–825.
Veselinovic et al., Chemical Abstracts, vol. 70, 1969 43583e.
Mikhel'son et al., Chemical Abstracts, vol. 70, 1969 81509t.
Ogata et al., Chemical Abstracts, vol. 74, 1971 26398p.
Vol'pin Chemical Abstracts, vol. 81, 1974 1011992.
Stolyarov et al., Chem. Abstracts, vol. 68 18292k.

*Primary Examiner*—Natalie Trousof
*Assistant Examiner*—Jane T. Fan

[57] ABSTRACT

A compound for the treatment of diseases which present an abnormal blood picture, comprising a complex combination of ascorbic acid, trivalent titanium and divalent copper, the ratio of the constituents of the complex compound being 36 moles ascorbic acid to 1.0 mole of trivalent titanium to 6 moles of divalent copper.

2 Claims, No Drawings

COMPLEX COMPOUND FOR THE TREATMENT OF DISEASES DISCLOSING ABNORMAL BLOOD PICTURES

The present invention relates to a complex compound which is useful in treating diseases, which by the persons suffering therefrom appear as abnormal blood pictures. Blood pictures from patients suffering from a number of diseases such as chronic polyarthritis, arteriosclerosis, manic-depressive psychosis, endogenous depressions, schizophrenia, cystic fibrosis, myopathies, amyotrophic lateral sclerosis disclose that abnormal blood pictures are also present in these cases, said pictures being normalized by treatment with the complex compound according to the invention, for which reason these diseases may be sensitive to the same treatment.

The compound according to the invention is also intended for use in the veterinary medicine.

During recent years cancer including leukemia and in certain cases chronic polyarthritis has been treated with cytostatica which are chemical compounds effective on the cell division and compounds with a drastic toxicity. The treatment is prolonged and because of the toxicity attented with very serious side effects.

It has been assumed that lack of minerals in human fullblood plays a decisive part for the existence of cancer and chronic polyarthritis in man.

It has now been ascertained that patients suffering from the above diseases have an abnormal blood picture, especially with regard to the elemental balance found in full-blood of healthy human beings. By spectroscopic analysis of the contents of elements in full-blood a characteristic picture of leukemia cancer is thus found, there being the same deviations from the normal contents for 13 different compounds and the size of the deviations being related to the gravity of the disease.

It has been ascertained that a change in the composition of the full-blood towards normal results in an improved state of health.

The compound according to the invention comprises a complex combination of ascorbic acid, trivalent titanium, and divalent copper, the ratio of the constituents of the complex compound being 36 mol ascorbic acid to 1 mol $Ti^{+++}$ to 6 mol $Cu^{++}$.

The said complex compound is a brown, amorphous solid, m.p. 170° C., with a spicy odour. It is easily soluble in water, difficult to dissolve in 96% ethanol and insoluble in diethylether.

The metal constituent usually comes from the salts: $Ti_2(SO_4)_3$, $TiCl_3$, $CuSO_4$ and $CuCl_2$, which are readily dissociable, physiologically acceptable salts.

The novel compound is usually administered in the form of an aqueous solution or as powder or tablets. Administration in tablet form is preferred. The novel compound may be administered together with additional components, e.g. the auxiliaries usual in the galenic pharmacy and other medicaments which do not influence the compound of the invention in a disadvantageous direction. Oral administration is suitable.

To an adult patient the daily dosage of the composition according to the invention is e.g. 100–200 mg.

By treating a patient suffering from leukemia with 200 mg a day of the complex compound according to the invention as the only treatment the patient has in spite of all experience been kept alive for 2 years, and a considerable improvement of the general condition and an improvement of the result of the spectrum analysis have been obtained.

By repeated tests with mice suffering from leukemia significant positive results have been obtained by treatment with the compound according to the invention, the mortality of the control groups being two or three times the mortality of the treated groups.

After treatment during 3 to 4 months with the compound according to the invention, 3 patients suffering from chronic polyarthritis disclosed a marked normalization of the blood pictures, and they all disclosed a marked improvement in the form of highly reduced pains.

After treatment with the compound according to the invention a patient suffering from myopathy disclosed a marked normalization of the blood picture.

A mouse suffering from a heavy abdominal liquid extravasation owing to cancer (verified by dissection) was treated with the compound according to the invention. After 14 days, the extravasation vanished completely.

Two mice, both suffering from a $2 \times 2$ cm mammary cancer (verified by biopsy adenocarcinom), were treated with the compound according to the invention for 13 weeks. The tumour of the first mouse could not be macroscopically detected after these 13 weeks, and the tumour of the second mouse had shrunken to $1 \times 1$ cm.

The preparation of the compound according to the invention is illustrated but not limited by the following examples:

EXAMPLE 1

12.8 ml 15% $Ti_2(SO_4)_3$ and 15 g $CuSO_4$, $5H_2O$ are added to an aqueous solution of 63 g concentrated ascorbic acid. 12 g BaO is then added for precipitation of the sulphate ion.

The mixture is stirred and the resulting precipitate is filtered off, whereupon the filtrate is evaporated under vacuum to yield a brown, amorphous, water soluble compound, m.p. 170° C.

EXAMPLE 2

A solution of 10 ml 15% $TiCl_3$, 63 g ascorbic acid and 10.2 g $CuCl_2$, $2H_2O$ in water is prepared. 16.8 g $Ag_2O$ is added to the resulting solution and the precipitate formed is filtered off, and the filtrate is freeze-dried to yield a brown, amorphous solid, m.p. 170° C.

The solid compound thus obtained is stable, however, an aqueous solution of the compound is unstable. The compound prepared according to the examples is a complex compound thus the copper ion cannot be precipitated with ammonia.

I claim:

1. A compound being a complex combination of ascorbic acid, trivalent titanium, and divalent copper, the ratio of the constituents of the complex compound being 36 mol ascorbic acid to 1 mol $Ti^{+++}$ to 6 mol $Cu^{++}$.

2. The compound according to claim 1, characterised in that it is a brown, amorphous solid with a spicy odour and a melting point of 170° C.